United States Patent
Brown et al.

[11] Patent Number: 6,068,615
[45] Date of Patent: *May 30, 2000

[54] INDUCTANCE-BASED DOSE MEASUREMENT IN SYRINGES

[75] Inventors: Stephen J. Brown, Mountain View, Calif.; Erik K. Jensen, Stockton, N.J.

[73] Assignee: Health Hero Network, Inc., Mountain View, Calif.

[ * ] Notice: This patent is subject to a terminal disclaimer.

[21] Appl. No.: 08/972,375

[22] Filed: Nov. 18, 1997

Related U.S. Application Data

[63] Continuation-in-part of application No. 08/681,290, Jul. 22, 1996, Pat. No. 5,782,814, which is a continuation-in-part of application No. 08/278,929, Jul. 22, 1994, Pat. No. 5,569,212.

[51] Int. Cl.[7] .................................................. A61M 5/00
[52] U.S. Cl. ............................................ 604/207; 73/149
[58] Field of Search ........................ 604/207–211, 65–67, 604/246, 407; 128/DIG. 1; 235/449–450; 222/23, 30; 73/861.11, 861.08, 149

[56] References Cited

U.S. PATENT DOCUMENTS

| | | | |
|---|---|---|---|
| 4,853,521 | 8/1989 | Claeys et al. | 235/375 |
| 4,950,246 | 8/1990 | Muller | 604/154 |
| 5,019,974 | 5/1991 | Beckers | 364/413.02 |
| 5,176,502 | 1/1993 | Sanderson et al. | 417/18 |
| 5,569,212 | 10/1996 | Brown . | |
| 5,704,922 | 1/1998 | Brown . | |
| 5,782,814 | 7/1998 | Brown et al. . | |
| 5,882,338 | 3/1999 | Gray . | |

*Primary Examiner*—Mark Bockelman
*Attorney, Agent, or Firm*—Black Lowe & Graham PLLC

[57] ABSTRACT

Measurements of insulin quantities in a syringe are performed inductively in an integrated insulin dose recorder/blood glucose meter. The syringe is placed in a holder before the administration of the dose, and the liquid quantity in the syringe is recorded. Inductors may be situated within the syringe and/or outside the syringe in various geometries. Standard or customized syringes may be used. Liquid quantities in the syringe are determined by comparing inductive response patterns of the syringe with calibration data stored in the device. Insulin dose and blood glucose histories are downloaded to a patient computer for transfer to a clinician's computer.

28 Claims, 5 Drawing Sheets

INDUCTANCE-BASED DOSE MEASUREMENT IN SYRINGES

RELATED APPLICATION DATA

This application is a continuation-in-part of U.S. patent application Ser. No. 08/681,290 entitled "Apparatus for Determining and Recording Injection Doses in Syringes Using Electrical Inductance Measurements," filed Jul. 22, 1996 now U.S. Pat. No. 5,782,814 which is a continuation-in-part of U.S. patent application Ser. No. 08/278,929 (now U.S. Pat. No. 5,569,212) filed Jul. 22,1994 now U.S. Pat. No. 5,569,212 and is related to U.S. patent application Ser. No. 08/591,308 filed Jan. 25, 1996 (now U.S. Pat. No. 5,628,309). This application is related to U.S. patent application Ser. No. 08/681,314, filed Jul. 22, 1996 now U.S. Pat. No. 5,720,733 and U.S. Ser. No. 08/898,711 filed Jul. 22, 1997 abandoned, as well as to the co-filed U.S. Patent Application entitled "Capacitance-Based Dose Measurements in Syringes" by inventors Stephen J. Brown and David R. L. Worthington. All of the above applications are assigned to the assignee of the present invention, and are herein incorporated by reference.

FIELD OF THE INVENTION

This invention relates to injection syringes and patient monitoring devices, and in particular to an apparatus for inductively determining and electronically recording doses of an agent delivered with an injection syringe.

BACKGROUND OF THE INVENTION

In recent years, the value of keeping electronic medical records in place of paper records has been widely recognized in the health care industry. The use of electronic medical records allows health care providers and patients to store, retrieve, and share medical information with considerably more ease and accuracy. The sharing of medical information is particularly important in treatment programs involving the injection of insulin, human growth hormone, or other medications.

Such injections are typically performed using disposable syringes. Unfortunately, no adequate apparatus exists for measuring and electronically recording dose information from a disposable syringe. As a result, the patient or health care worker performing the injection is burdened with the task of injecting the dose and then manually recording the dose amount in a log book.

Because of the frequency of such injections, often several times a day for diabetics, it can be difficult for a patient to keep accurate records. Indeed, studies have shown that a patient's own records and recollections are often incomplete and inaccurate. Additionally, a patient may intentionally cheat while making self-recorded entries in an attempt to create a log book that will please his or her doctor. In the long-term this makes patient monitoring extremely difficult and jeopardizes the treatment program, possibly even endangering the patient's life.

Attempts have been made at developing electronic management systems for assisting patients in self-administered drug programs. For example, U.S. Pat. No. 5,019,974 (Beckers) describes a hand-held, microprocessor-based recorder that interfaces with a master computer. The patient enters therapy information into the recorder via a keyboard. The recorder includes a display for displaying treatment therapy guidelines to the patient. The recorder also has a blood glucose meter for recording the patient's blood glucose levels.

The recorder described by Beckers does not automatically measure and record dose information from a disposable syringe. After injecting a dose, the patient must manually enter the dose information into the recorder using switches or keys. Although this is an improvement over keeping written records on paper, the effectiveness of the drug program is still limited by the patient's recollections and recordings, which are unreliable.

Attempts have also been made at developing devices that deliver a predetermined dose of medication and record the dose amount. For example, U.S. Pat. No. 5,176,502 (Sanderson et al.) describes a syringe pump for expelling a preset dose of medication from a syringe. The syringe pump includes a syringe retainer for holding the syringe and a driver for engaging the plunger of the syringe. An electric motor pushes the driver and plunger into the syringe barrel to expel the medication.

The syringe pump further includes a monitoring circuit for monitoring the motion of the driver during the delivery of the medication. The monitoring circuit includes a linear potentiometer having an electrically conductive strip of resistive material. The resistive material is positioned such that it engages an electrical contact of the driver. The position of the electrical contact on the resistive strip varies the voltage of the monitoring circuit, thus indicating the position of the plunger inside the barrel. A microprocessor receives voltage signals from the monitoring circuit and compares the voltage signals to preprogrammed signals to determine if the plunger displacement corresponds to correct displacement for delivering the preset dose. A control mechanism connected to the microprocessor regulates the driver's movement to ensure the preset dose of medication is delivered.

Although the syringe pump described by Sanderson et al. allows electronic recording of dose information, it is only designed to deliver medication directly into an intravenous line. It is not designed to inject a patient directly nor can it measure and record a dose from a syringe unless the syringe pump pushes the plunger. Consequently, the syringe pump is of little use to a health care worker who must inject a patient directly, or to an outpatient who must follow a self-injection treatment program.

Another device for injecting a preset dose of medication and for recording the injected dose is disclosed in U.S. Pat. No. 4,950,246 issued to Muller. Muller describes a battery-operated injection pen having a pump rod driven by an electric motor. The electric motor is controlled by an electronic control unit that includes a microprocessor with a memory for storing dose information. The injection pen further includes a sensor connected to the control unit for electrically determining the position of the pump rod, and thus the amount of medication injected.

Although the injection pen described by Muller measures and electronically records dose information, it has several disadvantages that have precluded its widespread use. The injection pen is an expensive device requiring complicated electronic equipment to deliver and record doses. Moreover, because the injection pen integrates a syringe and electronic recorder into one device, it is not disposable. The patient must use it repeatedly for each injection, even after the injection pen has been contaminated with blood. Consequently, the injection pen does not provide an inexpensive, convenient, or hygienic solution to patients wishing to measure and electronically record injected dose information.

U.S. Pat. No. 4,853,521 issued to Ronald Claeys presents a programmable, intelligent reader unit which receives and records drug data using hand-held or fixed scanners. The scanners read bar codes in place on syringes, ampules, flow meters, etc. In addition, this intelligent reader allows the user to weigh a syringe before and after injection to determine and record the administered amount of medicine. Dosage data logged in this manner can be displayed or printed out in the form of a record.

Operating the device described by Ronald Claeys requires many complicated steps of weighing syringes, scanning in bar codes, etc. The complexity of the required procedures as well as the high cost of the apparatus have precluded its widespread use. Additionally, the device cannot be easily carried by the user for recording doses while away from the health care facility or home. Thus, no inexpensive apparatus exists for determining and electronically recording dose information from a disposable syringe. Further, no such apparatus exists that is both simple in operation and easily carried by a user.

OBJECTS AND ADVANTAGES OF THE INVENTION

It is a primary object of the present invention to provide an apparatus for inductively determining and electronically recording an injection dose delivered from a disposable syringe. It is another object of the invention to provide an apparatus that may be easily operated and carried by a user. A further object of the invention is to suit the apparatus to diabetic patients, and to diabetes home care in particular. It is yet another object to provide an apparatus facilitating automated paperless data processing, from the measurement performed by the patient to the recording at the clinic. These and other objects and advantages will become more apparent after consideration of the ensuing description and drawings.

SUMMARY OF THE INVENTION

An apparatus for inductively measuring and electronically recording a dose delivered using a syringe comprises: a holder for receiving and holding a syringe in a measurement position; an inductive element coupled to the holder and enclosing the syringe such that an inductive response of the inductive element is indicative of the dose when the syringe is in the measurement position; a measuring device connected to the inductive element for measuring inductive responses of the inductive element; and a recording device connected to the measuring device for recording a dose datum indicative of the inductive response and thus indicative of the dose.

Preferably, the holder comprises a well laterally enclosing the syringe when the syringe is in the measurement position. The inductor is then coupled to the well such that the inductor laterally encloses the syringe when the syringe is in the measurement position. It is preferred that the syringe comprises an inductance-enhancing element whose position relative to the syringe barrel is indicative of the dose, and whose position determines the inductive response of the inductive element. The inductance-enhancing element preferably comprises a ferromagnetic or ferrimagnetic longitudinal plunger element embedded in a plastic shell to form the syringe plunger. The inductance-enhancing element preferably comprises a ferrite strip, but may comprise a ferromagnetic core filling the plunger cross-section almost entirely, or a series of longitudinally-spaced, stacked disks arranged within the plunger. Alternatively, a conventional syringe having a plunger consisting essentially of a plastic rod may be used.

A port connected to the recording device is used to download data stored in the recording device to an external storage or communication device such as a host computer. Also connected to the recording device is a testing device for testing a physical condition of the patient and generating condition data representative of the physical condition. The recording device records the condition data. Preferably, the testing device is a blood glucose meter and the physical condition is the patient's blood glucose level. A display connected to the measuring device is used to display recorded doses and blood glucose levels to the patient. A computing device is connected to the recording device. The computing device computes dose data from measured inductive responses and stored calibration data, for storage in the recording device. Dose data preferably comprises administered doses. The calibration data, stored in a calibration memory device, is indicative of the correspondence between inductive responses and dose data for the particular syringe used by the patient. The calibration data generated by measuring inductive responses for the entire range of potential liquid quantities in the syringe, and recording the correspondence between liquid quantities and inductive responses.

A housing encloses the measuring and recording devices, and preferably encloses and magnetically shields the inductive element. The holder is mechanically coupled to the housing. The housing is sufficiently compact to be hand-held and carried by a user. The inductive element preferably consists of a single inductor, and the inductive response preferably comprises the inductance of the inductor. In an alternative embodiment, the inductive element comprises plural longitudinally-spaced inductors, and the inductive response comprises an inductive response pattern.

In one embodiment, the inductor is situated within the syringe barrel and is connected to input and output terminals on the outside of the syringe. The housing then comprises a contact field coupled to the outside of the housing. The contact field comprises an input contact for contacting the input terminal, and an output contact for contacting the output terminal.

DESCRIPTION OF THE FIGURES

FIG. 3-A shows a perspective view of an alternative apparatus of the present invention.

FIG. 3-B shows a longitudinal sectional view of a syringe suitable for use with the apparatus of FIG. 3-A.

FIG. 3-C shows a transverse sectional view of the syringe of FIG. 3-B.

FIG. 5-A shows a longitudinal section view of a multi-inductor element of the present invention.

FIG. 5-B shows a longitudinal section view of another multi-inductor element of the present invention.

FIG. 6-A illustrates qualitatively the dependence of inductance with plunger displacement for the geometry shown in FIG. 2.

FIG. 6-B illustrates qualitatively the dependence of inductance with plunger displacement for each inductor in the geometry of FIG. 5-A.

DETAILED DESCRIPTION

Figure 1:
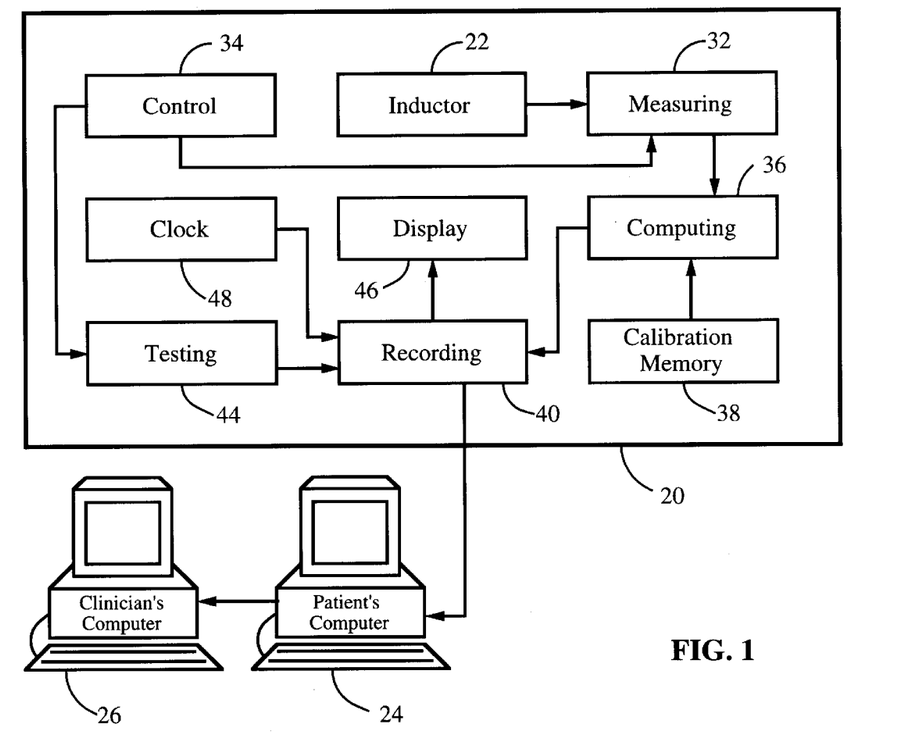
FIG. 1 is a high-level schematic diagram illustrating the structure of a preferred apparatus of the present invention.

FIG. 1-A is a high-level schematic diagram illustrating a preferred apparatus 20 of the present invention. Apparatus 20 records data indicative of doses delivered to a patient using a syringe. Apparatus 20 is capable of downloading the recorded data to a patient computer 24, which in turn is capable of communicating with a clinician's computer 26 over a long-distance communication line such as a telephone line or the Internet.

Apparatus 20 comprises an inductive element 22 enclosing at least part of the syringe. Inductive element 22 comprises one or more inductors arranged in a predetermined spatial relationship. A measuring device 32 is in electrical communication with inductive element 22, and detects an inductive response of inductive element 22 when the syringe is in a predetermined measurement position. Measuring device 32 preferably comprises a LC circuit with a resonant frequency $\omega=1/\sqrt{LC}$. Inductance-measuring devices are well known in the art. The inductive response of inductive element 22 is indicative of the quantity of liquid in the syringe, and consequently of the dose administered to the patient using the syringe. A control device 34 is in electrical communication with measuring device 32, and temporally controls the operation of measuring device 32. Control device 34 is capable of turning-on measuring device 32 when the syringe is in the measurement position, for example before the administration of the dose to the patient. Control device 34 preferably comprises a button which the patient can press to trigger a measurement.

A computing device 36 is in electrical communication with measuring device 32 and with a calibration memory 38. Computing device 36 preferably comprises a microprocessor. Computing device 38 is further in electrical communication with a recording device 40. Recording device 40 preferably comprises a memory chip. Computing device 36 generates dose data to be stored in recording device 40. The dose data preferably comprises a dose (e.g. insulin dose) administered to the patient, but may be in general any data which can be used to reconstruct (for example within apparatus 20, at patient computer 24, or at clinician computer 26) the dose administered to the patient. In particular, computing device 36 calculates the quantity of liquid within the syringe before injection of a dose, or the difference between the liquid quantities within the syringe before and after injection. Computing device 36 then sends the result (the dose) to recording device 40 for storage.

Computing device 36 determines liquid quantities by comparing inductive response data received from measuring device 32 with predetermined calibration data stored in calibration memory 38. The calibration data is indicative of the correspondence between inductive responses and liquid quantities for the entire range of potential liquid quantities in the syringe. That is, calibration memory 38 stores the liquid quantity corresponding to a given inductive response of inductive element 22, for all liquid quantities potentially present in the syringe.

A testing device 44 is electrically connected to recording device 40. Testing device 44 tests a physical condition of the patient, and generates condition data representative of the physical condition. Preferably, the physical condition is diabetes, the testing device comprises a conventional blood glucose meter, and the condition data comprises a blood glucose level of the patient. Recording device 40 records the condition data generated by testing device 44. A display 46 is electrically connected to recording device 40, and displays dose data and condition data to the patient. Display 46 is preferably a conventional liquid crystal display (LCD). A display such as display 46 may be in general directly connected to computing device 36 and testing device 44, rather than indirectly through recording device 40. A digital clock 48 is connected to recording device 40. Upon prompting, clock 48 sends the current date and time to recording device 40 for recording in conjunction with dose or condition data.

Figure 2:
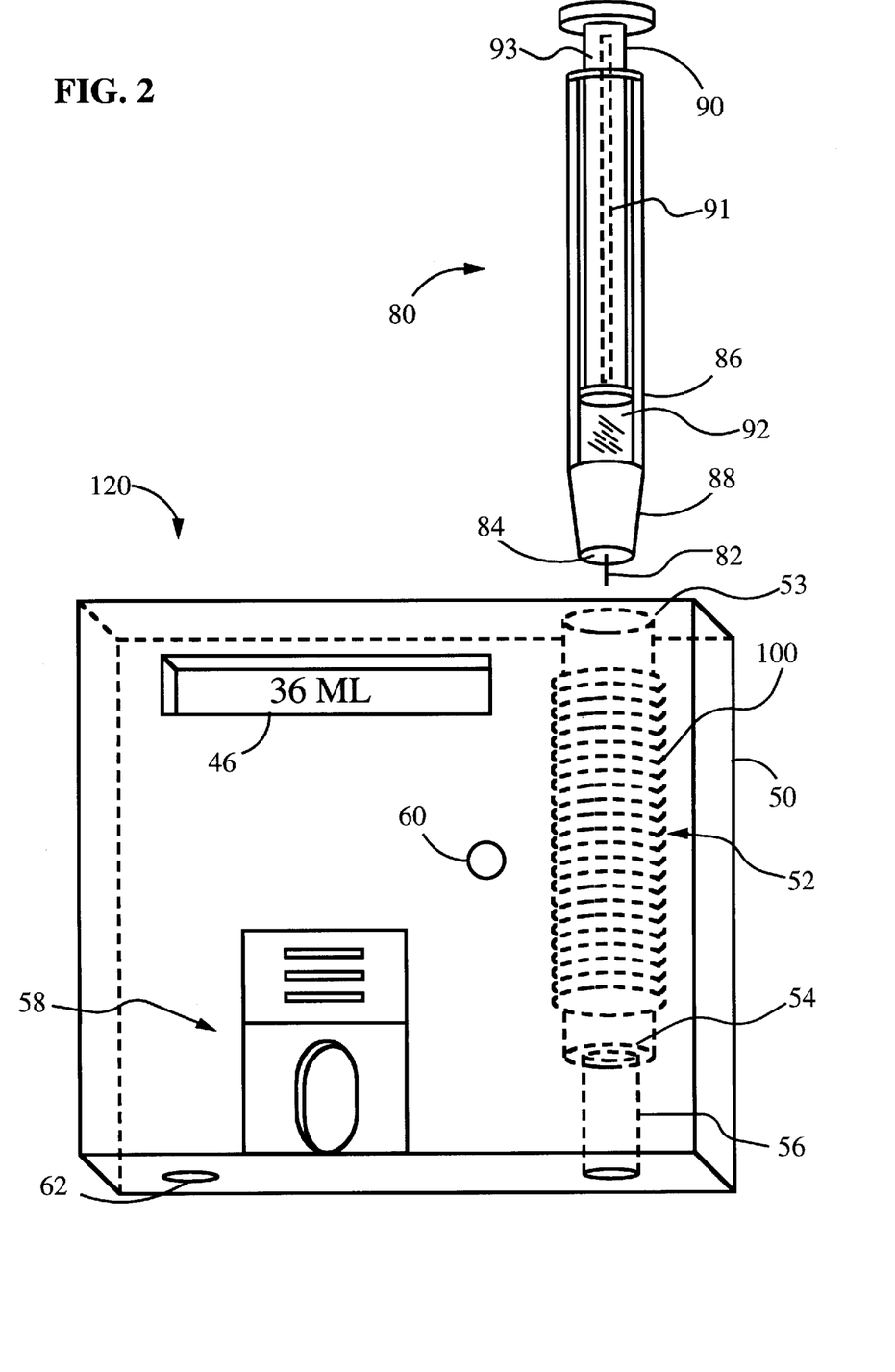
FIG. 2 shows a perspective view of a preferred apparatus and syringe of the present invention.

FIG. 2 shows a perspective view of an apparatus 120, according to a preferred embodiment of the present invention. Apparatus 120 comprises a housing 50 enclosing the various electronic components of apparatus 120. Housing 50 preferably comprises a metal layer for magnetically shielding internal components of apparatus 120, in particular inductive components (see below). Housing 50 is sufficiently compact to allow apparatus 120 to be hand-held and carried by a user. Apparatus 120 has dimensions on the order of centimeters (<20 cm), and a weight not exceeding hundreds of grams.

Display 46 is recessed within housing 50. A patient interface 58 of testing device 44 is also coupled to housing 50. The patient places his or her finger on patient interface 58, allowing testing device 44 to perform a blood glucose measurement for the patient. Blood glucose meters are well known in the art and will not be discussed here in detail. A dose measurement control 60 of control device 34 is coupled to housing 50, and allows the patient to specify when dose measurements are to be performed by apparatus 120 (see below). A port 62 allows data transfer between recording device 40 and patient computer 24.

Housing 50 also encloses a holder 52 for receiving and holding a syringe 80 in the measurement position. Syringe 80 corresponds specifically to the calibration data stored in calibration memory 38. A circular opening 53 within housing 50 provides access to holder 52. Holder 52 has a well-like shape for laterally enclosing syringe 80. Holder 52 defines an enclosed space 56 opposite opening 53, for accommodating a needle 82 of syringe 80 when syringe 80 is in the measurement position. Enclosed space 56 is preferably closed off, so as to prevent accidental access to needle 82 in the measurement position.

Syringe 80 comprises a barrel 86 and a plunger 90, defining a space for a liquid 92. Plunger 90 preferably comprises a longitudinal strip 91 made of a ferromagnetic material such as ferrite, embedded in a plastic body 93. Alternatively, a standard syringe with a plunger consisting of a plastic body can be used with a device of the present invention. Plunger 90 is capable of longitudinal motion relative to barrel 86, for adjusting the volume available to liquid 92. Holding device 52 comprises an alignment ledge 54 for aligning barrel 86 to holder 52 in the measurement position. A contact surface 84 of syringe 80 is in contact with alignment ledge 54 when syringe 80 is in the measurement position.

A cylindrical inductor 100 is mechanically coupled to holder 52, and encloses syringe 80 externally and laterally. Inductor 100 encloses syringe 80 along the entire longitudinal extent along which the position of plunger 90 and/or the quantity of liquid 92 may vary. The position of plunger 90 and/or the quantity of liquid 92 within syringe 80 determine the inductance of inductor 100. The magnetic permeabilities of plunger 90 and liquid 92 are substantially different, such that the inductance of inductor 100 is indicative of the position of plunger 90 relative to inductor 100 and of the quantity of liquid 92 within syringe 80. In particular, the two permeabilities differ by at least a factor of two, preferably by a factor of ten or more.

To operate apparatus 120, a patient inserts the manufacturer-provided syringe 80 in holder 52 prior to administration of the dose. When syringe 80 is pressed against alignment ledge 54, syringe 80 is in the measurement position. The patient presses the button 60 to activate measuring device 32. Measuring device performs measurement of the inductance of inductor 100. Computing device 36 then determines the liquid quantity within syringe 80. Recording device 40 then records the liquid quantity as the administered dose, in conjunction with the current date and time obtained from clock 48. Recording device 40 may also record condition data received from testing means 44, and the associated date and time. Recording device 40 then contains the patient's blood glucose and insulin dose histories. The patient periodically (e.g. weekly) connects his or her apparatus 120 to patient computer 24 and downloads the histories stored in recording device 40. The histories are then periodically transmitted to clinician's computer 26.

Figure 3:
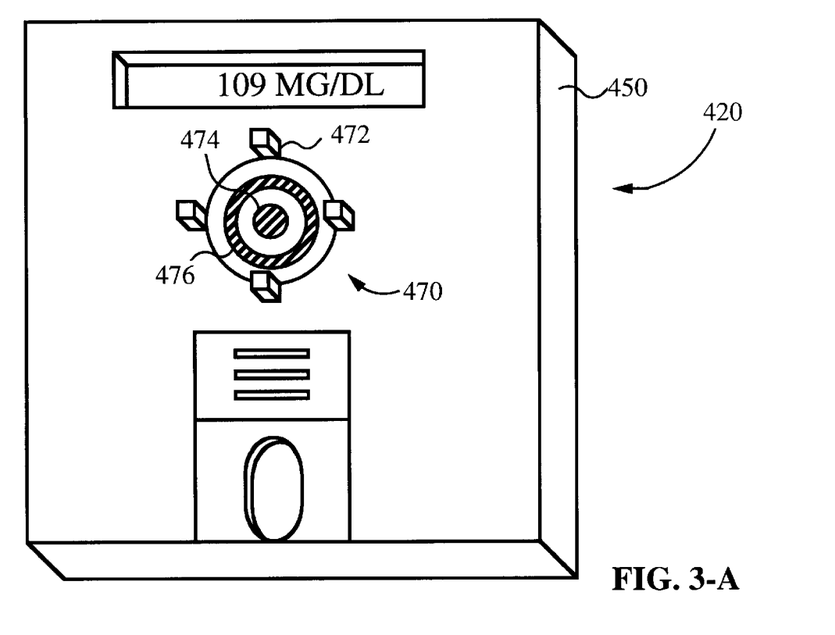

FIG. 3-A shows a perspective view of an alternative apparatus 420 of the present invention, suitable for measuring doses using inductors situated within syringes. A circular placement field 470 is delineated on the outside of a housing 450 of apparatus 420. Placement field 470 is bordered on four sides by a set of rigid positioning studs 472 forming a holder. Placement field 470 includes a circular input contact 474 positioned at the center of field 470 and a ring-shaped output contact 476 positioned concentrically to input contact 474. Input contact 474 and output contact 476 are made of an electrically conductive material, preferably copper, and are connected to measuring device 32.

FIG. 3-B shows a longitudinal sectional view of a syringe 480 suitable for use with the apparatus of FIG. 3-A, while FIG. 3-C shows a transverse sectional view of syringe 480. Syringe 480 comprises a plunger 490 positioned within a barrel 486. Plunger 490 comprises a cylindrical ferromagnetic core 491 encapsulated within a plastic shell 493. Plunger 490 also comprises a cylindrical cap 478 sized so as to fit on placement field 470 between studs 472 when syringe 480 is in a measurement position. Cap 478 comprises an input terminal 412 and an output terminal 414 situated such that input terminal 412 and output terminal 414 are in electrical communication respectively with input contact 474 and output contact 476 when syringe 480 is in the measurement position. Barrel 486 comprises an inductor 400 encapsulated within a plastic side wall. Metallic contact lines 403, 405 within plunger 490 and barrel 486 establish electrical communication between inductor 400 and input terminal 412 and output terminal 414, respectively. For taking a measurement, the patient places syringe 480 on placement field 470 and activates measuring device 32 to measure the inductance of inductor 400.

Figure 4:
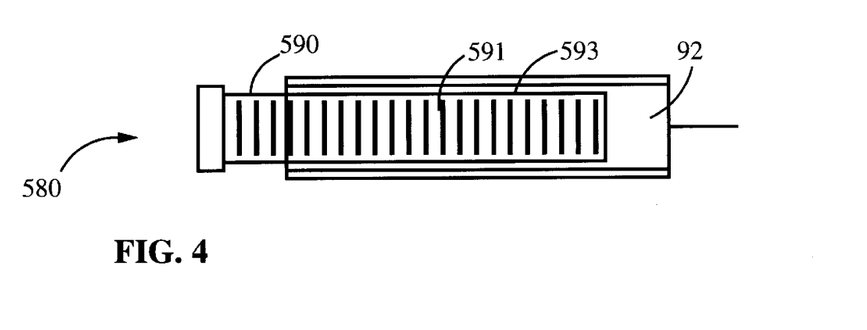
FIG. 4 shows a longitudinal sectional view of an inductance-enhanced syringe of the present invention.

FIG. 4 shows a longitudinal sectional view of an alternative geometry for an inductance-enhanced syringe 580 of the present invention. A plunger 590 of syringe 580 comprises an inductance-enhancing element 591 comprising a plurality of longitudinally-spaced distinct segments 595, embedded in a plastic shell 593. Segments 595 are thin ferromagnetic disks stacked along the longitudinal direction of plunger 590. Segments 595 have a magnetic permeability substantially higher than that of plastic shell 593 or liquid 92.

Figure 5:
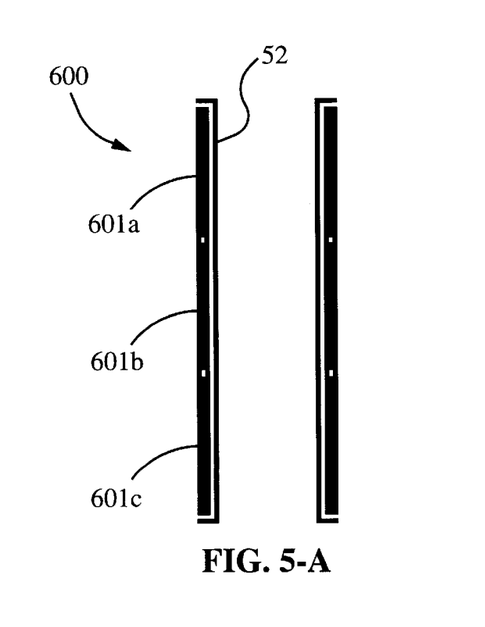

FIGS. 5-A and 5-B illustrate an alternative inductor geometry of the present invention. An inductive element 600, coupled to and enclosing holder 52, is formed by a plurality of independent longitudinally-spaced, stacked inductors 601a–c. Measuring device 32 is used to measure an inductive response pattern of inductors 601. The response pattern preferably consists of the inductance of each inductor 601. The longitudinal extent of each inductor 601a–c is much greater than the desired resolution achievable with inductive element 600. In the embodiment illustrated in FIG. 5-B, the longitudinal extent of each inductor 801 of an inductive element 800 is of the same order of magnitude as the desired resolution to be achieved with inductive element 800. The use of plural longitudinally-stacked inductors reduces the vulnerability of a system of the present invention to dosage determination errors caused by a constant inductance offset.

Figure 6:
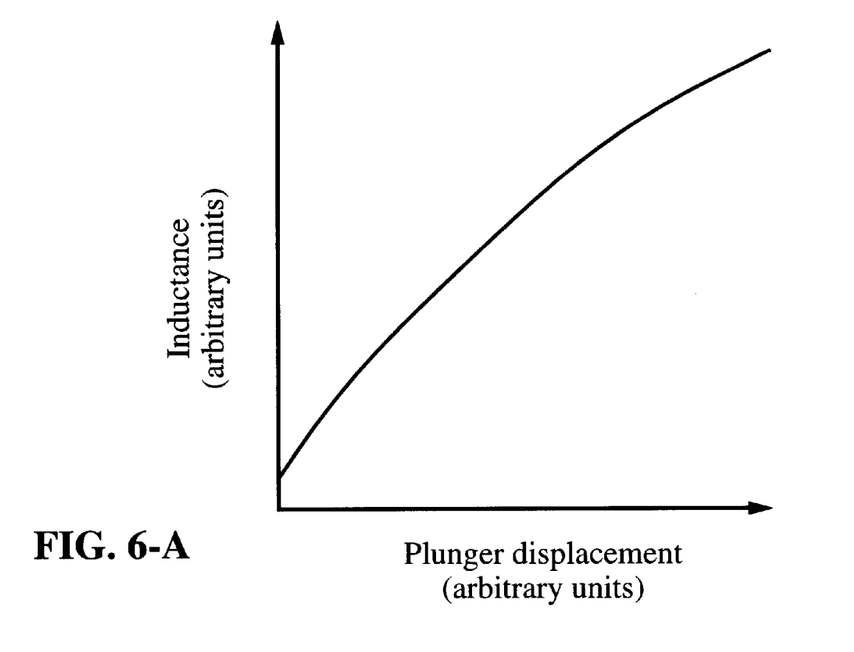

FIGS. 6-A and 6-B illustrate qualitatively the variation of inductance with plunger displacement for the inductive element geometries of FIGS. 2 and 5-A, respectively. In FIGS. 6-A and 6-B, the plunger is taken to have a higher effective magnetic susceptibility than the liquid in the syringe. The inductance of inductor 100 increases with the extent of plunger 90 enclosed by inductor 100, as illustrated in FIG. 6-A. The plunger displacement and delivered dose are computed from the measured inductance and stored calibration data. Likewise, the response pattern of inductive element 600 changes as more of plunger 90 becomes enclosed by inductive element 600. For a large dose to be delivered (small plunger displacement), plunger 90 is enclosed only by inductor 601a but not by inductors 601b–c. For a small dose to be delivered (large plunger displacement, or plunger pushed in close to the syringe needle), plunger 90 is completely enclosed by inductors 601a–b and only partially enclosed by inductor 601c.

The following discussion is intended to illustrate the invention, and should not be construed to limit the invention. Consider a geometry similar to those shown in FIGS. 2 or 3-B, for a typical or inductance-enhanced syringe. Consider a position of the plunger in which an inductor encloses a length x of liquid and a length D-x of plunger (see FIG. 3-B). From the inductance of an ideal long solenoid of length D, cross-sectional area A, and turn density (number of turns per unit length) n, $$L = \mu n^2 D A, \quad [1]$$

one can obtain an order-of-magnitude estimate of the total inductance of the inductor as a function of x. Neglecting edge effects, $$L_{tot} \approx L_{liq} + L_{plg} \approx n^2 A(\mu_{liq} x + \mu_{plg}(D-x)) = n^2 A(x(\mu_{liq} - \mu_{plg}) + \mu_{plg} D), \quad [2]$$

where $\mu_{liq}$ and $\mu_{plg}$ are magnetic permeabilities, and $L_{liq}$ and $L_{plg}$ are inductances corresponding respectively to the liquid and the plunger. As illustrated by eq. [2], the sensitivity of $L_{tot}$ to variations in x increases with the difference between the magnetic permeabilities of the plunger and the liquid.

For a ferromagnetic-core plunger and corresponding solenoid, n is on the order of $10^5$ m$^{-1}$, A is on the order of $10^{-5}$ m$^2$, and $\mu_{liq}$ and $\mu_{plg}$ are, respectively, on the order of $10 \mu_o$ for water and $>10^3 \mu_o$ for a typical ferromagnetic or ferrimagnetic material. The above values yield a sensitivity on the order of $10^2$ mH per mm of plunger displacement. The inductor sensitivity may be lower for a ferrite-strip plunger or for a conventional plastic plunger. The inductor sensitivity may also be lower for other inductor geometries. The corresponding sensitivity of the inductance-measuring device may be adjusted according to the particular inductor geometry and plunger used; generally a more sensitive measuring device will be needed for measuring displacements of plungers having an effective permeability closer to that of the liquid.

It will be clear to one skilled in the art that the above embodiments may be altered in many ways without departing from the scope of the invention. Generally, the dose data may include, for example, quantities of liquid in the syringe before and/or after the administration of the dose, or inductive response values before and/or after the administration of the dose; the patient's and/or the clinician's computers then determine the dose administered to the patient from the dose data stored in the recording device. In such an embodiment, calibration data may be stored on the patient's or clinician's computer, and the apparatus may lack a computing device. The patient computer need not be a conventional personal computer, but can be in general any data storage device or device allowing communication between the patient's measurement apparatus and the clinician's data storage device or server. An apparatus of the present invention may connect directly to a clinician's server, rather than indirectly through a patient computer. Various computation and storage devices used in the present invention may generally be implemented through software or dedicated hardware, or combinations thereof. For a multiple-delivery injection device such as an injection pen, liquid quantities before and after each injection are measured and the administered dose is taken to be the difference between the two quantities. The present invention is not limited to diabetes care, and may be used for monitoring patient compliance with any injection-based treatment program.

Various inductive element geometries and placements may be suitable in a device of the present invention. In particular, the inductive element need not laterally enclose the syringe completely or even partially, as long as the inductive element is inductively coupled to the syringe. The method does not require the presence of a plunger to determine inductance; a method of the present invention may be used to inductively measure liquid levels in plungerless injection devices operated using air pressure, for example.

Accordingly, the scope of the invention should be determined by the following claims and their legal equivalents.

What is claimed is:

1. An apparatus for inductively measuring and electronically recording a dose delivered from a syringe, comprising:
   a) a holder for receiving and holding said syringe in a measurement position;
   b) at least one inductive element positioned on said holder such that an inductive response generated from said inductive element is indicative of said dose when said syringe is in said measurement position;
   c) a measuring device in communication with said inductive element, for measuring said inductive response; and
   d) a recording device in communication with said measuring device, for recording a dose datum indicative of said inductive response, whereby said dose datum is indicative of said dose.

2. The apparatus of claim 1 further comprising a port in communication with said recording device, for transmitting said dose datum from said recording device to a host computer.

3. The apparatus of claim 1 further comprising a testing device for testing a physical condition of a patient and for generating a condition datum representative of said physical condition, said testing device being connected to said recording device such that said recording device records said condition datum.

4. The apparatus of claim 3 wherein said testing device comprises a blood glucose meter and said condition datum comprises a blood glucose level.

5. The apparatus of claim 1 further comprising a display connected to said measuring device, for displaying said dose to a patient administering said dose.

6. The apparatus of claim 1 wherein said recording device comprises a digital memory unit.

7. The apparatus of claim 1 further comprising a computing device in communication with said recording device, for computing said dose datum from said inductive response.

8. The apparatus of claim 7 further comprising a calibration memory device in communication with said computing unit, for providing said computing device with calibration data indicative of a correspondence between said inductive response and said dose datum.

9. The apparatus of claim 7 wherein said dose datum comprises said dose.

10. The apparatus of claim 1 further comprising a housing enclosing said measuring device and said recording device, wherein said holder is mechanically coupled to said housing.

11. The apparatus of claim 10 wherein said housing encloses said holder and said at least one inductive element, for magnetically shielding said inductive element and said syringe when said syringe is in said measurement position.

12. The apparatus of claim 10 wherein said housing is sufficiently compact to be hand-held and carried by a patient.

13. The apparatus of claim 1 comprising a plurality of longitudinally-spaced inductors such that said inductive response comprises an inductive response pattern of said plurality of inductors.

14. The apparatus of claim 1 wherein said holder comprises a well for laterally enclosing said syringe in said measurement position.

15. The apparatus of claim 1 wherein said syringe comprises a barrel, a plunger and a second inductive element attached to said syringe.

16. The apparatus of claim 15 wherein said second inductive element is attached to said plunger such that a position of said plunger generates said inductive response.

17. The apparatus of claim 15 wherein said second inductive element comprises a ferromagnetic material.

18. The apparatus of claim 15 wherein said second inductive element comprises a ferromagnetic plunger core.

19. The apparatus of claim 18 wherein said second inductive element comprises a plurality of sections arranged longitudinally on said syringe.

20. A diabetes monitoring and insulin dose recording apparatus for recording an insulin dose from a syringe, said apparatus comprising:
   a) a holder for receiving and holding a syringe containing insulin in a measurement position;
   b) an inductive element positioned on said holder such that an inductive response of said inductive element is indicative of an insulin quantity within said syringe when said syringe is in said measurement position;
   c) a measuring device in communication with said inductive element, for measuring said inductive response;
   d) a computing device in communication with said measuring device, for computing from said inductive response a dose datum indicative of an insulin dose delivered to a patient using said syringe;
   e) a blood glucose meter for determining a blood glucose datum indicative of a blood glucose level of said patient; and
   f) a recording device in communication with said computing unit and said blood glucose meter, for recording said dose datum and said blood glucose datum.

21. The apparatus of claim 20 further comprising a port connected to said recording device, for transmitting said dose datum and said blood glucose datum from said recording device to a host computer.

22. The apparatus of claim 21 further comprising a display connected to said measuring device, for displaying said insulin dose and said blood glucose level to said patient.

23. An apparatus for inductively measuring and electronically recording a dose delivered using a syringe, said apparatus comprising:
   a) a syringe with a barrel portion said syringe comprising an input terminal, and output terminal and an inductive element for generating an inductive response indicative said dose;
   b) a housing enclosing a measuring device and a recording device; and
   c) a field coupled to said housing, comprising:
      an input contact for contacting an input terminal of a syringe when said syringe is in a measurement position, and
      an output contact for contacting an output terminal of said syringe when said syringe is in said measurement position; wherein
         said input terminal and said output terminal are connected said inductive element such that an inductive response of said inductive element is indicative of said dose,
         said input contact and said output contact are connected to said measuring device such that said measurement device is capable of measuring said inductive response when said input terminal contacts said input contact and said output terminal contacts said output contact, and
         said recording device is connected to said measuring device, for recording a dose datum indicative of said inductive response, whereby said dose datum is indicative of said dose.

24. An inductance-enhanced syringe comprising:
   a) a barrel for holding a liquid to be delivered with said syringe;
   b) a plunger movably positioned within said barrel, for expelling said liquid through a needle coupled to said barrel, wherein:
      said plunger comprises an inductance-enhancing element, and
      a position of said inductance-enhancing element relative to said barrel is indicative of a quantity of said liquid within said syringe.

25. A method of monitoring a dose administered to a patient using a syringe, comprising the steps of:
   a) measuring an inductive response of an inductive element inductively coupled to said syringe such that the inductive response varies in accordance with position of the syringe plunger within the syringe, wherein said inductive response is indicative of said dose; and
   b) electronically recording a dose datum indicative of said inductive response, whereby said dose datum is indicative of said dose.

26. The method of claim 25 wherein said dose comprises an insulin dose.

27. A method of calibrating an apparatus for inductively measuring and electronically recording a dose delivered using a syringe, comprising the steps of:
   a) placing a syringe in a holder;
   b) measuring a plurality of inductive responses of an inductive element enclosing said syringe, wherein
      each of said plurality of inductive responses is indicative of a distinct predetermined liquid quantity in said syringe, and
      said plurality of inductive responses correspond to a range of potential liquid quantities in said syringe; and
   c) recording calibration data indicative of said plurality of inductive responses, whereby said calibration data establishes a correspondence between said plurality of inductive responses and liquid quantities within said range of potential liquid quantities in said syringe.

28. An apparatus for inductively measuring and electronically recording a dose, said apparatus comprising:
   a) a syringe comprising a barrel and a plunger;
   b) a holder with an inductive element positioned thereon, said holder for receiving and holding said syringe in a measurement position wherein said inductive element, and said syringe generate an inductive response indicative of said dose;
   c) a measuring device in communication with said inductive element, wherein said measuring device measures said inductive response; and
   d) a recording device in communication with said measuring device, for recording said dose.

* * * * *